(12) United States Patent
Barrera et al.

(10) Patent No.: US 11,331,161 B2
(45) Date of Patent: May 17, 2022

(54) SURGICAL ASSEMBLIES FACILITATING TISSUE MARKING AND METHODS OF USE THEREOF

(71) Applicant: COVIDIEN LP, Mansfield, MA (US)

(72) Inventors: Osvaldo Andres Barrera, Madison, CT (US); Kasey A. Grim, Boulder, CO (US); Joe D. Sartor, Longmont, CO (US)

(73) Assignee: Covidien LP, Mansfield, MA (US)

( * ) Notice: Subject to any disclaimer, the term of this patent is extended or adjusted under 35 U.S.C. 154(b) by 226 days.

(21) Appl. No.: 16/356,823

(22) Filed: Mar. 18, 2019

(65) Prior Publication Data

US 2019/0290386 A1   Sep. 26, 2019

Related U.S. Application Data

(60) Provisional application No. 62/647,185, filed on Mar. 23, 2018.

(51) Int. Cl.
| | | |
|---|---|---|
| A61B 90/00 | (2016.01) | |
| A61B 34/20 | (2016.01) | |
| A61B 17/32 | (2006.01) | |
| A61B 34/10 | (2016.01) | |

(52) U.S. Cl.
CPC ...... *A61B 90/39* (2016.02); *A61B 17/320068* (2013.01); *A61B 34/20* (2016.02); *A61B 90/37* (2016.02); *A61B 34/10* (2016.02); *A61B 2017/320073* (2017.08); *A61B 2090/3908* (2016.02); *A61B 2090/3983* (2016.02); *A61B 2090/3987* (2016.02); *A61B 2090/3991* (2016.02)

(58) Field of Classification Search
None
See application file for complete search history.

(56) References Cited

U.S. PATENT DOCUMENTS

| | | |
|---|---|---|
| 4,321,551 A | 3/1982 | Bleil et al. |
| 5,320,110 A | 6/1994 | Wang |
| 5,526,822 A | 6/1996 | Burbank et al. |
| 5,598,269 A | 1/1997 | Kitaevich et al. |
| 5,660,185 A | 8/1997 | Shmulewitz et al. |

(Continued)

FOREIGN PATENT DOCUMENTS

| | | |
|---|---|---|
| CN | 203001001 U | 6/2013 |
| EP | 1932481 A1 | 6/2008 |

(Continued)

OTHER PUBLICATIONS

International Search Report and Written Opinion, dated Jun. 21, 2017, corresponding to International Application No. PCT/US2017/028498; 11 total pages.

*Primary Examiner* — Colin T. Sakamoto

(57) ABSTRACT

A method of marking a tumor includes positioning a surgical instrument adjacent breast tissue, generating an image of a tumor in the breast tissue on a display using an ultrasonic probe of the surgical instrument, aligning a needle of the surgical instrument with the tumor using the image of the tumor generated on the display, deploying the needle from the ultrasound probe into the breast tissue, and deploying an elongated tissue marker from the needle into the tumor, thereby fixing a distal portion of the tissue marker in the tumor.

22 Claims, 15 Drawing Sheets

(56) References Cited

U.S. PATENT DOCUMENTS

| | | | |
|---|---|---|---|
| 5,751,869 A | 5/1998 | Li et al. |
| 5,810,541 A | 9/1998 | Casey et al. |
| 5,810,841 A | 9/1998 | McNeirney et al. |
| 5,855,554 A | 1/1999 | Schneider et al. |
| 5,976,092 A | 11/1999 | Chinn |
| 6,007,497 A | 12/1999 | Huitema |
| 6,069,748 A | 5/2000 | Bietry |
| 6,086,544 A | 7/2000 | Hibner et al. |
| 6,102,866 A | 8/2000 | Nields et al. |
| 6,203,498 B1 | 3/2001 | Bunce et al. |
| 6,273,862 B1 | 8/2001 | Privitera et al. |
| 6,364,839 B1 | 4/2002 | Little et al. |
| D461,895 S | 8/2002 | Barnes et al. |
| 6,428,487 B1 | 8/2002 | Burdorff et al. |
| 6,471,651 B1 | 10/2002 | Hwang et al. |
| 6,582,368 B2 | 6/2003 | Holdaway et al. |
| 6,605,095 B2 | 8/2003 | Grossman |
| 6,688,758 B2 | 2/2004 | Thibault |
| 6,689,067 B2 | 2/2004 | Sauer et al. |
| 6,692,200 B2 | 2/2004 | Peterson |
| 6,702,749 B2 | 3/2004 | Paladini et al. |
| 6,752,768 B2 | 6/2004 | Burdorff et al. |
| 6,945,942 B2 | 9/2005 | Van Bladel et al. |
| 7,024,791 B2 | 4/2006 | Marshall et al. |
| 7,031,367 B2 | 4/2006 | Marshall et al. |
| 7,041,058 B2 | 5/2006 | Piehler |
| 7,269,907 B2 | 9/2007 | Levine et al. |
| 7,303,530 B2 | 12/2007 | Barnes et al. |
| 7,310,887 B2 | 12/2007 | Nash et al. |
| 7,367,945 B2 | 5/2008 | Dasgupta et al. |
| 7,416,533 B2 | 8/2008 | Gellman et al. |
| 7,722,549 B2 | 5/2010 | Nakao |
| 7,858,038 B2 | 12/2010 | Andreyko et al. |
| 8,162,852 B2 | 4/2012 | Norris |
| 2002/0007130 A1* | 1/2002 | Burbank .......... A61B 17/00491 600/564 |
| 2002/0173719 A1 | 11/2002 | Zhao et al. |
| 2003/0014010 A1 | 1/2003 | Carpenter et al. |
| 2003/0069502 A1 | 4/2003 | Makin et al. |
| 2003/0199753 A1 | 10/2003 | Hibner et al. |
| 2003/0199754 A1 | 10/2003 | Hibner et al. |
| 2003/0199785 A1 | 10/2003 | Hibner et al. |
| 2004/0034280 A1 | 2/2004 | Privitera et al. |
| 2004/0077972 A1 | 4/2004 | Tsonton et al. |
| 2004/0106934 A1 | 6/2004 | Grossman |
| 2004/0109823 A1* | 6/2004 | Kaplan ................ A61L 31/04 424/1.11 |
| 2004/0249278 A1 | 12/2004 | Krause |
| 2005/0065453 A1 | 3/2005 | Shabaz et al. |
| 2005/0131291 A1 | 6/2005 | Floyd et al. |
| 2006/0144548 A1 | 7/2006 | Beckman et al. |
| 2006/0200041 A1 | 9/2006 | Weikel et al. |
| 2007/0049822 A1 | 3/2007 | Bunce et al. |
| 2007/0149878 A1 | 6/2007 | Hankins |
| 2007/0167736 A1 | 7/2007 | Dietz et al. |
| 2007/0232953 A1 | 10/2007 | Dietz et al. |
| 2008/0015429 A1 | 1/2008 | Tsonton et al. |
| 2008/0146915 A1 | 6/2008 | McMorrow |
| 2009/0326412 A1 | 12/2009 | Pakter |
| 2010/0174185 A1* | 7/2010 | Wang .................. A61B 8/14 600/437 |
| 2011/0087132 A1 | 4/2011 | DeFreitas et al. |
| 2011/0125055 A1 | 5/2011 | Privitera et al. |
| 2011/0313288 A1* | 12/2011 | Chi Sing ............. A61B 8/481 600/437 |
| 2011/0319759 A1 | 12/2011 | Liu et al. |
| 2012/0078238 A1* | 3/2012 | Carr, Jr. .............. A61B 5/6842 606/1 |
| 2012/0323253 A1* | 12/2012 | Garai .................. A61N 1/057 606/129 |
| 2017/0296294 A1* | 10/2017 | Hermann .......... A61B 17/3468 |
| 2017/0303889 A1* | 10/2017 | Grim ................ A61B 10/0283 |

FOREIGN PATENT DOCUMENTS

| WO | 2008120137 A1 | 10/2008 |
|---|---|---|
| WO | 2009067740 A1 | 6/2009 |
| WO | 2015193917 A2 | 12/2015 |

\* cited by examiner

SURGICAL ASSEMBLIES FACILITATING TISSUE MARKING AND METHODS OF USE THEREOF

CROSS-REFERENCE TO RELATED APPLICATION

This application claims the benefit of and priority to U.S. Provisional Application No. 62/647,185, filed on Mar. 23, 2018, the entire contents of which are incorporated by reference herein.

BACKGROUND

Technical Field

The present disclosure relates to tissue marking and, more particularly, to tissue markers and methods for tissue marking and handling.

Description of Related Art

To treat breast cancer, two of the most common procedures are a mastectomy, which involves the complete removal of the breast tissue, and a lumpectomy which involves the removal of only the tumor and the immediately surrounding tissue. When possible, a lumpectomy is usually the preferred operation since lumpectomies are less invasive, less painful, and conserve most of the patient's breast.

The current standard of care for lumpectomy is the guide wire: prior to performing a lumpectomy, a tissue marker—often referred to as a "wire"—is positioned so that one end of the wire is in the target tissue and the other end sticks out of the breast to be used as a guide for the surgeon during a lumpectomy. In some cases, the wires may be placed inaccurately, or they can migrate between the time of placement and the time of surgery, causing the surgeon to cut through the tumor causing carcinogenic cell dissemination. This can also result in a painful pre-operative procedure and/or involve intricate logistics such as the schedule coordination of a radiologist and a surgeon.

SUMMARY

Provided in accordance with the present disclosure is a method of marking a tumor. The method includes positioning a surgical instrument adjacent breast tissue, generating an image of a tumor in the breast tissue on a display using an ultrasonic probe of the surgical instrument, aligning a needle of the surgical instrument with the tumor using the image of the tumor generated on the display, deploying the needle from the ultrasound probe into the breast tissue, and deploying an elongated tissue marker from the needle into the tumor, thereby fixing a distal portion of the tissue marker in the tumor.

Some methods may further include generating an image of the tumor with the elongated tissue marker fixed therein.

Some methods may further include planning a surgical excision of the tumor based on a position of a first depth marking on the elongated tissue marker relative to an outer periphery of the tumor.

Some methods may further include excising the tumor at a location adjacent a second depth marking of the elongated tissue marker. The second depth marking may be disposed proximally of the first depth marking.

The method may further include retracting the needle from the breast tissue and into the ultrasonic probe.

In methods, the retraction of the needle may cause the tissue marker to deploy from the needle.

In methods, the tissue marker may be deployed from the needle prior to the needle being retracted.

The method may further include transitioning a plurality of fixation elements of the tissue marker from a collapsed state into an expanded state, in which the fixation elements anchor into the tumor.

In methods, the fixation elements may transition toward the expanded state automatically upon deployment from the needle.

In methods, the fixation elements may be fabricated from shape memory material, such that the fixation elements transition toward the expanded configuration in response to heat from the breast tissue.

In methods, the fixation elements may be resiliently biased toward the expanded configuration and maintained in the collapsed configuration by the needle.

In methods, the fixation elements may transition toward the expanded configuration by moving an actuator coupled to the plurality of fixation elements.

In methods, the actuator may be moved distally to transition the fixation elements toward the expanded configuration.

The method may further include determining a distance between an access opening in the breast tissue and a distal tip of the tissue marker using a plurality of longitudinally-extending segments disposed along a length of the tissue marker. Each of the segments may have a discrete visually identifying feature.

In another aspect of the present disclosure, a method of marking a tumor is provided and includes generating an image of a tumor in the breast tissue using an ultrasonic probe, aligning an elongated tissue marker with the tumor using the image of the tumor, deploying the tissue marker from the ultrasonic probe into the tumor, and transitioning a plurality of fixation elements of the tissue marker from a collapsed state into an expanded state to fix a distal portion of the tissue marker in the tumor.

Some methods may further include retracting an outer member of the tissue marker from the breast tissue.

In methods, the retraction of the outer member of the tissue marker may allow the plurality of fixation elements to transition toward the expanded state.

In methods, the plurality of fixation elements may be fabricated from shape memory material, such that the plurality of fixation elements transition toward the expanded configuration in response to heat from the breast tissue.

In methods, the plurality of fixation elements may be resiliently biased toward the expanded configuration and maintained in the collapsed configuration by the outer member.

In methods, the plurality of fixation elements may transition toward the expanded state automatically upon deployment from a needle of the ultrasonic probe.

In yet another aspect of the present disclosure, a method of marking a tumor includes inserting an elongated tissue marker into a tumor disposed in breast tissue, and transitioning a plurality of fixation elements of the tissue marker from a collapsed state into an expanded state. In the expanded state, the plurality of fixation elements anchor a distal portion of the tissue marker in the tumor.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Various aspects and features of the present disclosure are described hereinbelow with references to the drawings, wherein.

DETAILED DESCRIPTION

Figure 1:
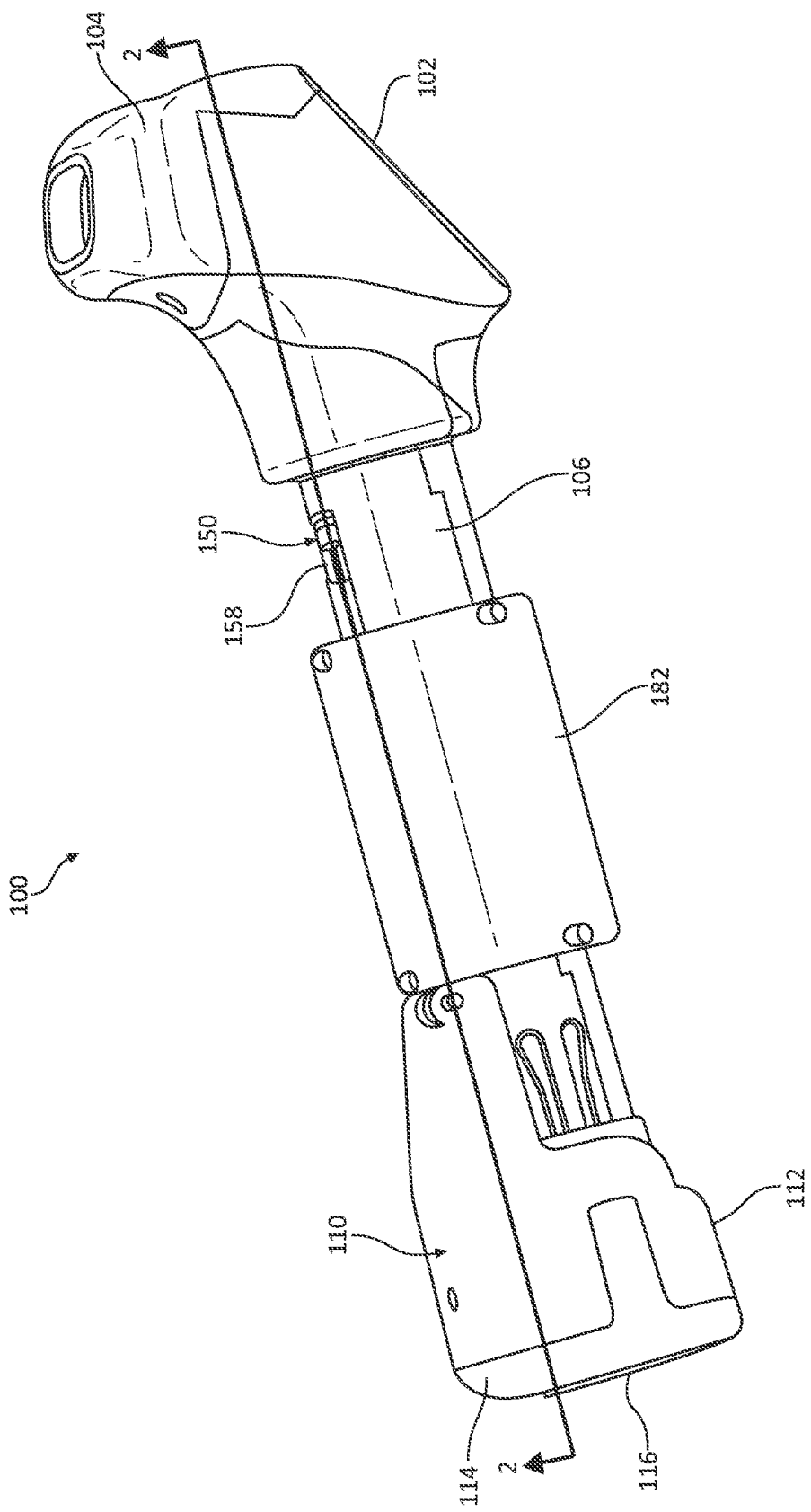
FIG. 1 is a perspective view of a surgical instrument for marking tissue in accordance with the present disclosure.

Surgical assemblies facilitating tissue marking and methods for using the surgical assemblies for marking tissue (e.g., a tumor) are provided in accordance with the present disclosure and described in detailed below. In embodiments, the surgical assembly includes a surgical instrument having an ultrasonic probe for positioning a needle of the surgical instrument in line with target tissue. A tissue marker of the surgical assembly is disposed within the needle and deployable therefrom. In some embodiments, the tissue marker may be deployable from the ultrasonic probe without using a needle. The tissue marker may include a plurality of fixation elements that protrude radially outward from a distal tip of the tissue marker upon being deployed from the needle of the surgical instrument and into the target tissue. The tissue marker may have a greater stiffness than conventional markers. The tissue marker may further have a plurality of colored markings for providing a visual indication of the tissue depth of the tissue marker.

Detailed embodiments of such surgical assemblies facilitating tissue marking and methods using the same are described below. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in virtually any appropriately detailed structure.

With reference to FIGS. 1-16B, a surgical assembly 10 (FIG. 11) is provided in accordance with the present disclosure for marking a selected portion of tissue, such as, for example, a lesion, including, but not limited to, a tumor located in breast tissue. The surgical assembly 10 includes a surgical instrument 100 (FIGS. 1-11) and a tissue marker 200, 300, or 400 (FIGS. 11-16B) operably coupled to the surgical instrument 100.

With reference to FIGS. 1-10, the surgical instrument 100 of the surgical assembly 10 (FIG. 11) generally includes a display 102, an ultrasonic probe 110, and a needle assembly 160. The display 102 is disposed on a head 104 of the surgical instrument 100 and is in electrical communication with the ultrasonic probe 110 such that any information sensed by the ultrasonic probe (e.g., tissue structure) is displayed on the display 102. The head 104 may include a processor in communication with the display 102 and the ultrasonic probe 110 for processing the information sensed by the ultrasonic probe 110. In embodiments, the processor may be used to set the insertion depth of the needle assembly 160.

With specific reference to FIGS. 1-5, the surgical instrument 100 further includes a tubular shaft 106 extending distally from the head 104. In embodiments, the tubular shaft 106 may be monolithically formed with or integrally connected to the head 104. The tubular shaft 106 has a needle housing 108 fixed to a distal end portion thereof. The needle housing 108 includes a pair of stops 109a, 109b extending laterally outward from opposite sides thereof.

Figure 5:
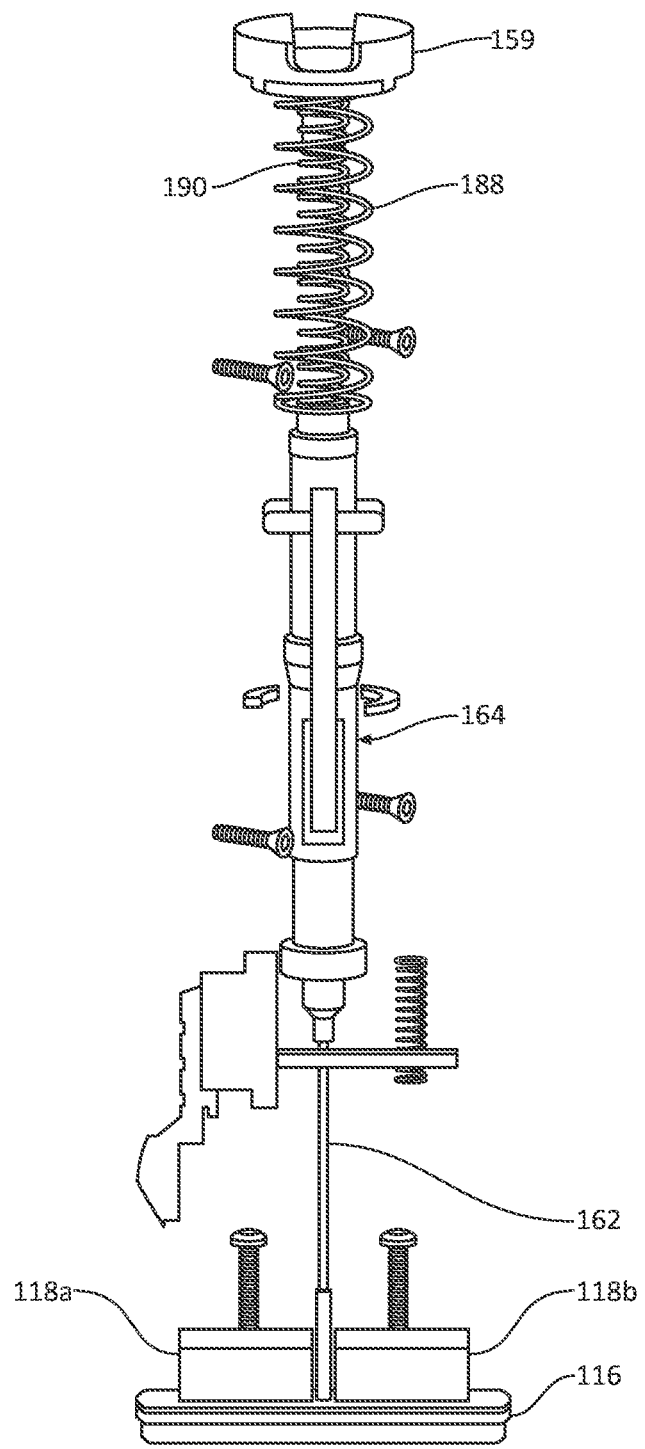
FIG. 5 is a front view, with some parts removed, of the surgical instrument of FIG. 1.
Figure 6:
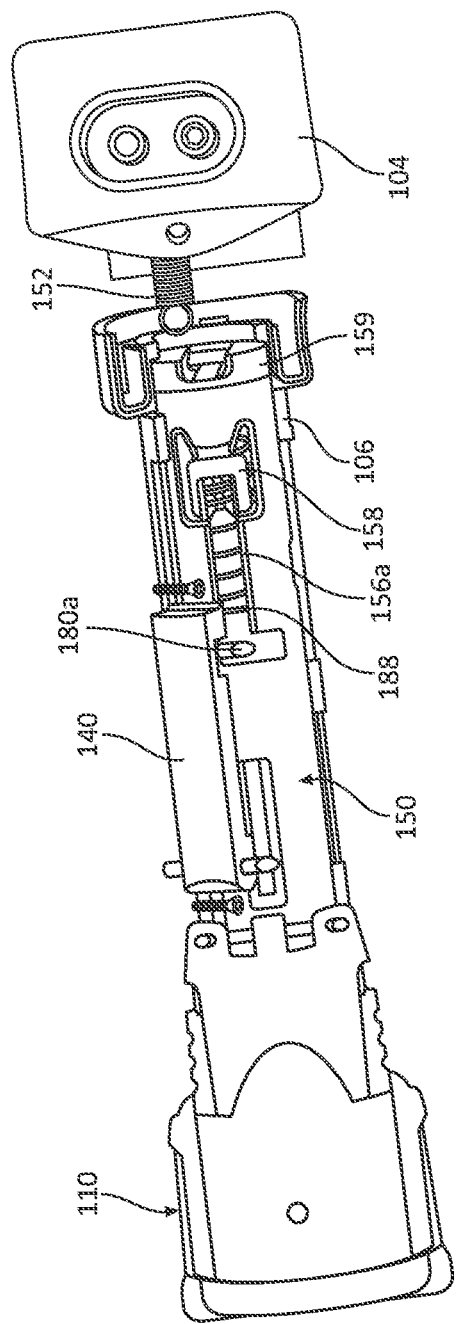
FIG. 6 is a perspective view, with some parts removed, of the surgical instrument of FIG. 1.

The ultrasonic probe 110 includes a housing 112 pivotably coupled to the distal end portion of the tubular shaft 106 and an end cap 114 secured to the housing 112. The end cap 114 has a block 116 that supports a pair of ultrasonic sensors 118a, 118b (FIG. 5). The block 116 may be fabricated from silicone or any other suitable ultrasound-opaque material. The block 116 defines a central opening 120 therethrough configured for slidable receipt of a needle 162 of the needle assembly 160. The ultrasonic sensors 118a, 118b are in communication with the processor and/or the display 102 and are laterally spaced from one another to accommodate the needle 162 of the needle assembly 162 therebetween. In this way, the needle 162 may be moved through the ultrasonic probe 110 without inhibiting its function.

Figure 8:
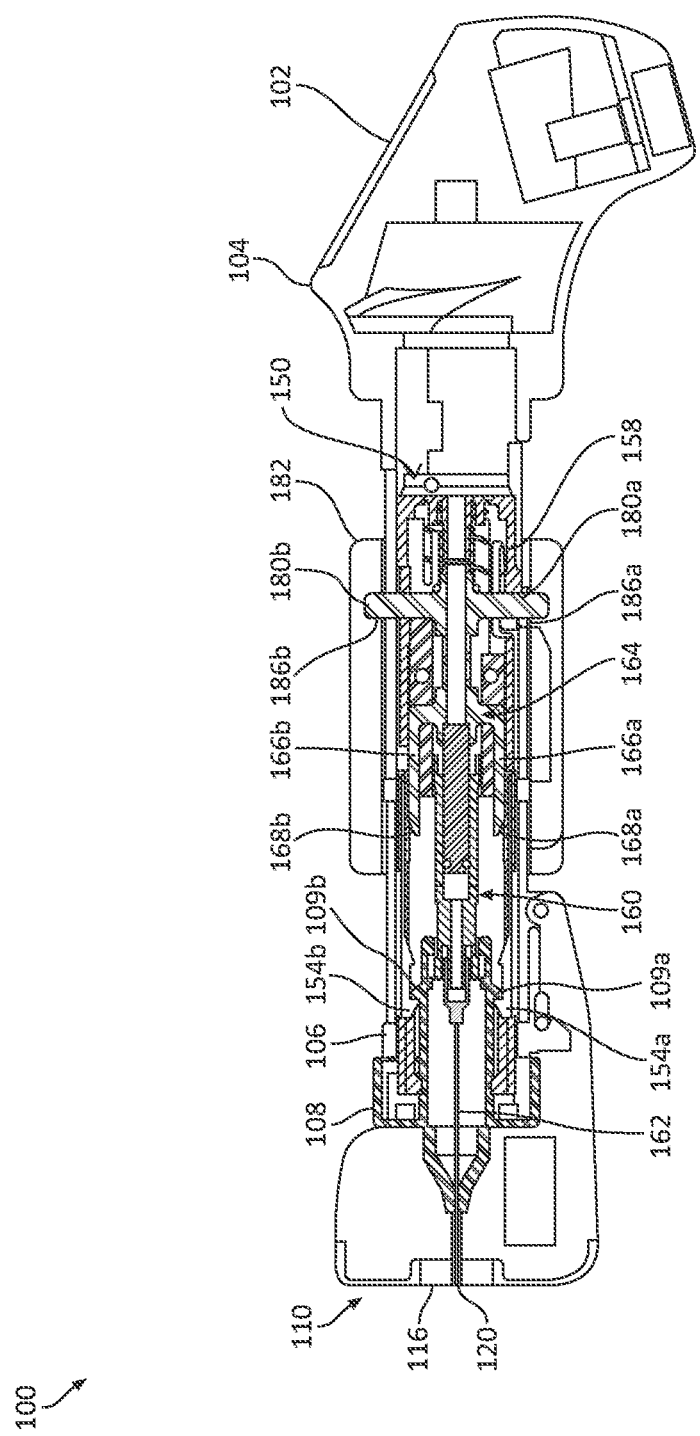
FIG. 8 illustrates the surgical instrument of FIG. 2 in a second pre-firing state.

Disposed within the tubular shaft 106 is an axially movable inner sheath 150. The inner sheath 150 is resiliently biased in a proximal direction by a biasing member 152 (e.g., an extension spring) that interconnects the inner sheath 150 and the head 104. The inner sheath 150 includes a pair of stops 154a, 154b located at a distal end portion thereof that matingly engage with the stops 109a, 109b of the needle housing 108 upon the inner sheath 150 moving from a proximal position (FIG. 4) to a distal position (FIG. 8). As such, when the inner sheath 150 is in the distal position, the inner sheath 150 is prevented from being retracted by the biasing member 152 toward the proximal position.

The inner sheath 150 defines a pair of longitudinally-extending channels 156a, 156b in an outer surface thereof. The channels 156a, 156b of the inner sheath 150 permit longitudinal movement of respective arms 180a, 180b of the needle assembly 160 therethrough. The inner sheath 150 includes a flexible locking member 158 located at a proximal end of one of the channels 156a, 156b. The locking member 158 of the inner sheath 150 is configured to releasably capture one of the arms 180a, 180b of the needle assembly 160 upon the needle assembly 160 entering a retracted position. The locking member 158 is adjacent an end of an actuator or trigger 140 (FIG. 6) of the surgical instrument 100. The actuator 140 is pivotably coupled to the tubular shaft 106 and is configured to flex or bend the locking member 158 of the inner sheath 150 inwardly to selectively disengage the locking member 158 of the inner sheath 150 from the one arm, e.g., arm 180a, of the needle assembly 160. As will be described in detail below, the inner sheath 150 functions to automatically retract the needle assembly 160 back to the retracted state after the needle assembly 160 is deployed.

The needle assembly 160 of the surgical instrument 100 generally includes a needle subassembly 164 and the needle 162 extending distally from the needle subassembly 164. In some embodiments, instead of having the needle 162 extending from the needle subassembly 164, the needle 162 of the needle assembly 160 may be replaced with one of the tissue markers 200, 300, 400 described below, which are deployable from the surgical instrument 100. The needle subassembly 164 includes a pair of distally-extending legs 166a, 166b each having a ramped distal end 168a, 168b. The ramped distal ends 168a, 168b of the legs 166a, 166b are configured to engage with the stops 154a, 154b of the inner sheath 150 upon the needle assembly 160 moving distally into the deployed position. As will be described in greater detail below, as the ramped distal ends 168a, 168b of the legs 166a, 166b engage the respective stops 154a, 154b of the inner sheath 150, the stops 154a, 154b of the inner sheath 150 are forced radially outward and therefore out of engagement with the stops 109a, 109b of the needle housing 108.

The needle subassembly 164 further includes a pair of arms 180a, 180b extending radially outward of the inner sheath 150. The arms 180a, 180b are coupled to a collar 182 that is slidably attached to the tubular shaft 106 such that axial movement of the collar 182 along the elongated shaft 106 causes axial movement of the needle assembly 160. The collar 182 defines a pair of longitudinal tracks 184a, 184b therealong and a pair of circumferential notches 186a, 186b (FIG. 7) therein. The longitudinal tracks 184a, 184b and the circumferential notches 186a, 186b are each configured for selective receipt of the arms 180a, 180b of the needle subassembly 164. In one instance, when the arms 180a, 180b of the needle subassembly 164 are received in the respective tracks 184a, 184b of the collar 182, the needle subassembly 164 is axially movable through the tracks 184a, 184b and relative to the collar 182. In another instance, when the arms 180a, 180b of the needle subassembly 164 are received within the respective notches 186a, 186b (FIG. 7) defined in the collar 182 (due to a rotation of the collar 182), axial movement of the collar 182 causes the needle subassembly 164 to move with the collar 182.

The surgical instrument 100 includes a pair of needle actuators 188, 190 (e.g., springs) that extend between a proximal cap 159 of the inner sheath 150 and a proximal end of the needle subassembly 164. In embodiments, the surgical instrument 100 may include more or less than two needle actuators. The needle actuators 188, 190 resiliently bias the needle assembly 160 distally away from the proximal cap 159 of the inner sheath 150 toward a deployed position.

Figure 2:
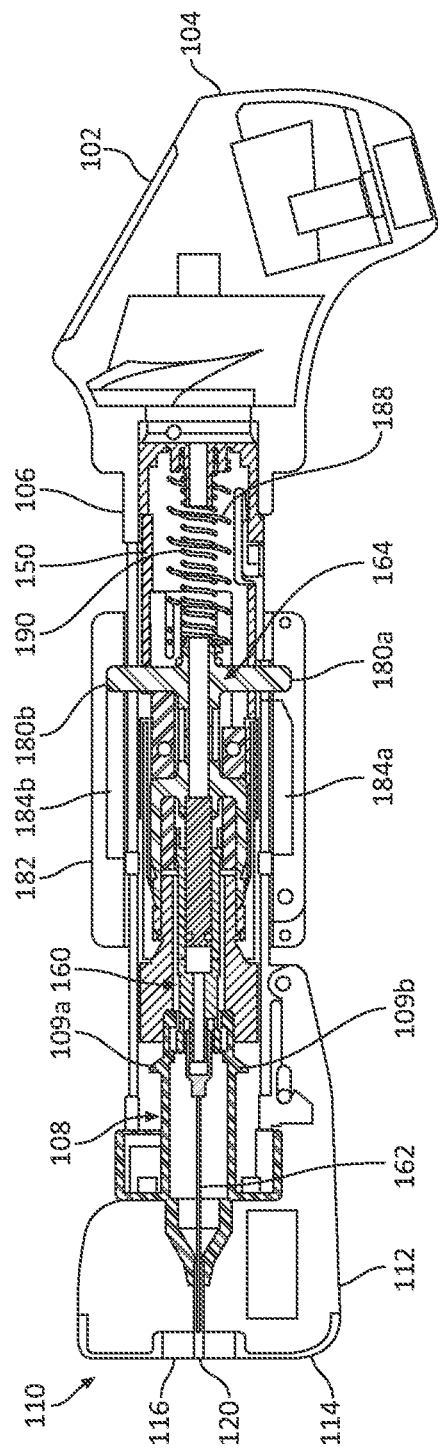
FIG. 2 is a cross-sectional view, taken alone line 2-2, of the surgical instrument of FIG. 1.
Figure 3:
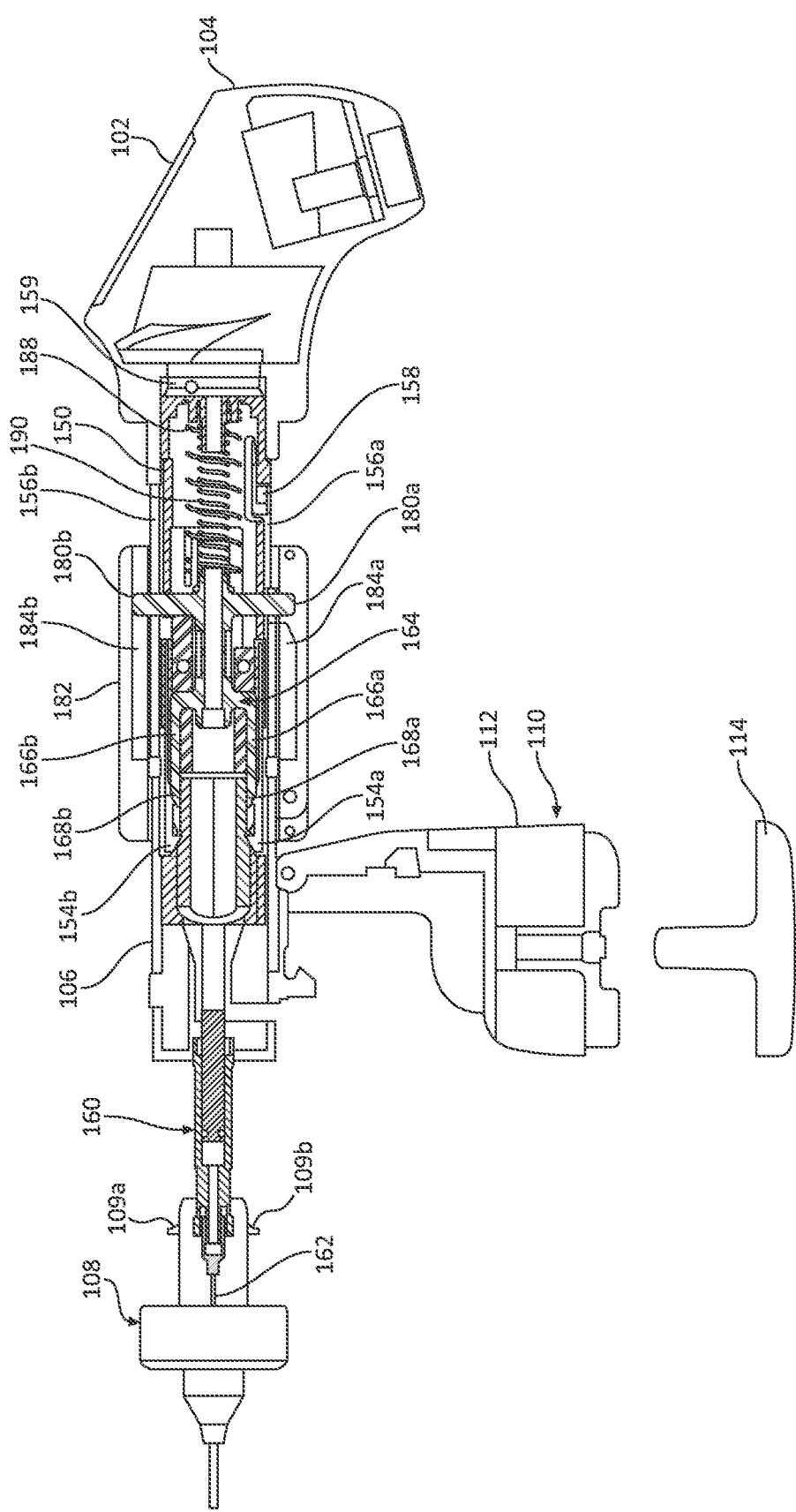
FIG. 3 illustrates the surgical instrument of FIG. 2 in a disassembled state.
Figure 4:
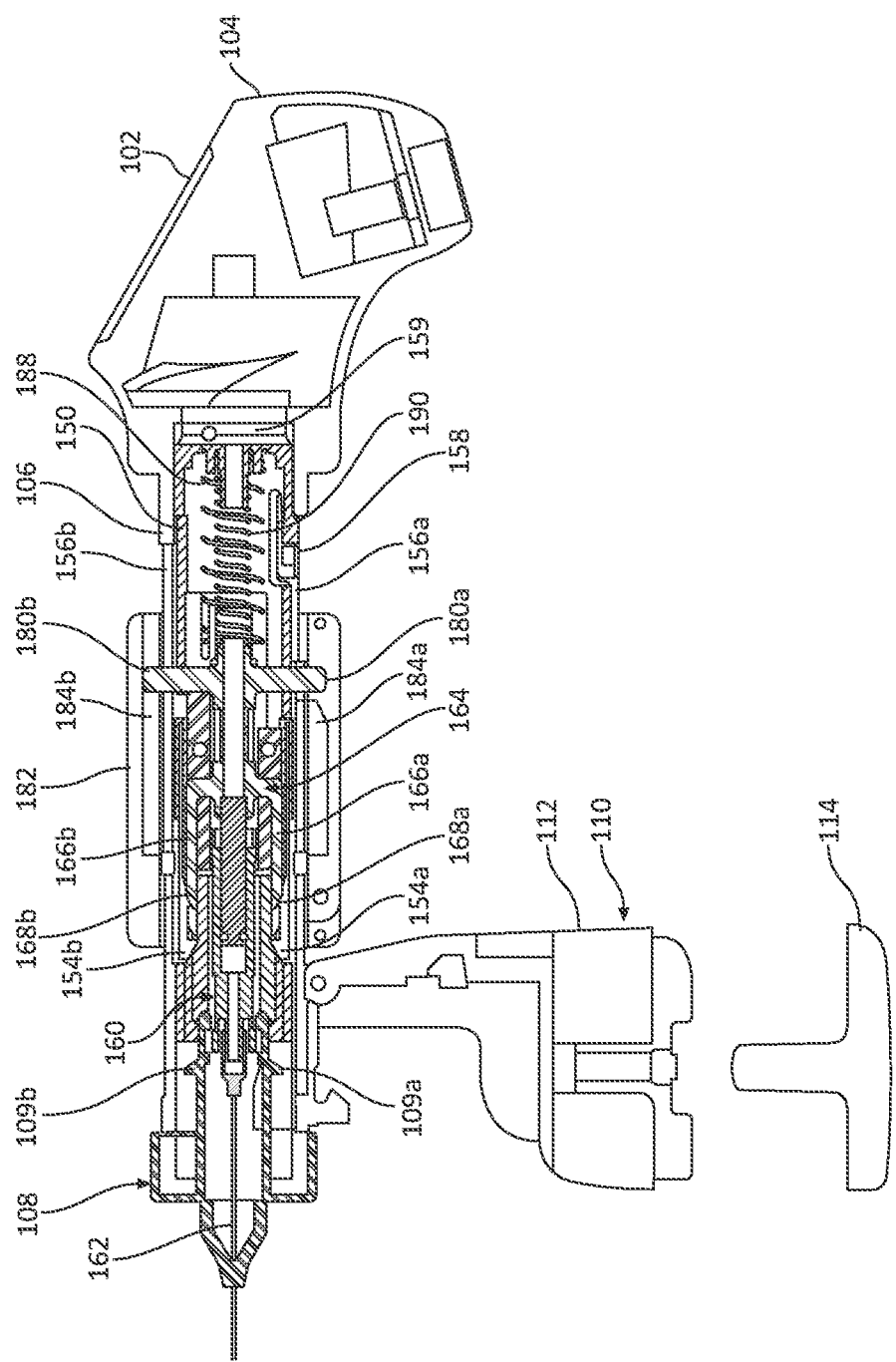
FIG. 4 illustrates the surgical instrument of FIG. 2 in a partially disassembled state.

An exemplary use of the surgical instrument 100 will now be described with reference to FIGS. 2 and 7-10. The surgical instrument 100 may be used to extract tissue samples from a lesion, for example, a tumor. With the needle 162 disposed within needle housing 108 in a position proximal to opening 120 in the ultrasonic probe 110, as shown in FIG. 2, the surgical instrument 100 is positioned such that the block 116 of the ultrasonic probe 110 is in abutting engagement with an outer surface of tissue (e.g., breast tissue). The ultrasonic sensors 118a, 118b (FIG. 5) of the ultrasonic probe 110 are activated to emit an ultrasonic field in a distal direction through the block 116 and toward the lesion. The ultrasonic sensors 118a, 118b then receive the reflected ultrasound waves and the processor of the surgical instrument 100 generates an image of the needle tip of the needle 162 and the lesion on the display 102. The surgical instrument 100 is moved relative to the target tissue until the needle tip is shown on the display 102 as being aligned with the target tissue.

Figure 7:
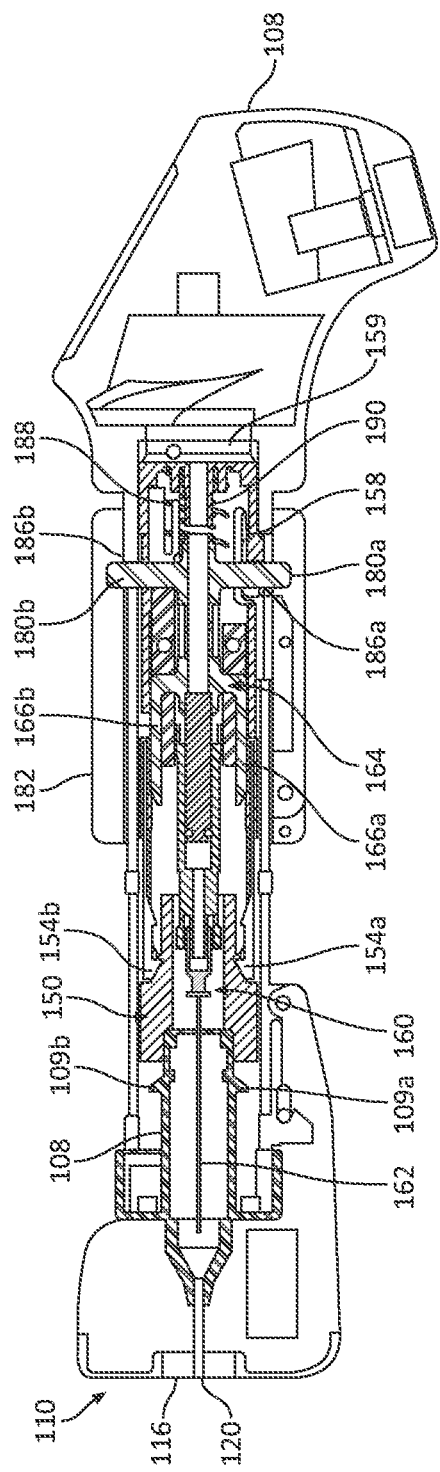
FIG. 7 illustrates the surgical instrument of FIG. 2 in a first pre-firing state.

With reference to FIGS. 2 and 7, with the needle 162 in the proper position, the surgical instrument 100 may be cocked in preparation for firing the needle assembly 160. To cock the needle assembly 160, the collar 182 is rotated relative to the arms 180a, 180b of the needle subassembly 164 to position the arms 180a, 180b of the needle assembly 164 in the notches 186a, 186b of the collar 182. With the arms 180a, 180b of the needle subassembly 164 captured in the notches 186a, 186b of the collar 182, proximal movement of the collar 182 along the tubular shaft 106 results in a retraction of the needle assembly 160 toward the proximal cap 159 of the inner sheath 150. Upon the needle subassembly 164 engaging the proximal cap 159 of the inner sheath 150, one of the arms 180a, 180b of the needle subassembly 164 is received in the flexible locking member 158 of the inner sheath 150 to lock together the needle assembly 160 and the inner sheath 150, as shown in FIG. 7. In addition to locking the needle assembly 160 with the inner sheath 150, proximal retraction of the needle assembly 160 within the tubular shaft 106 acts to compress the needle actuators 188, 190 between the needle subassembly 164 and the proximal cap 159 of the inner sheath 150.

To further prepare the surgical instrument 100 for firing, the collar 182 is advanced distally along the elongated shaft 106, which, in turn, drives distal advancement of the needle assembly 160 due to the arms 180a, 180b of the needle assembly 164 being captured in the notches 186a, 186b of the collar 182. As a result of arm 180a of the needle assembly 164 being in locking engagement with the locking member 158 of the inner sheath 150, as the needle assembly 160 moves distally, the inner sheath 150 follows. As the inner sheath 150 moves toward a distal position within the tubular shaft 106, the stops 154a, 154b of the inner sheath 150 pass over and interlock with the stops 109a, 109b of the needle housing 108, as shown in FIG. 8. Since the needle housing 108 is fixed relative to the tubular shaft 106, the proximal force applied to the inner sheath 150 by the biasing member 152 (FIG. 6) will not result in proximal movement of the inner sheath 150 back toward the retracted position. As such, the collar 182, the needle assembly 160, and the inner sheath 150 are each prevented from moving proximally out of the position shown in FIG. 8. In this pre-fired position, the needle 162 is held within the opening 120 defined in the block 116 of the ultrasonic transducer 110 without protruding distally from the ultrasonic probe 110.

Figure 9:
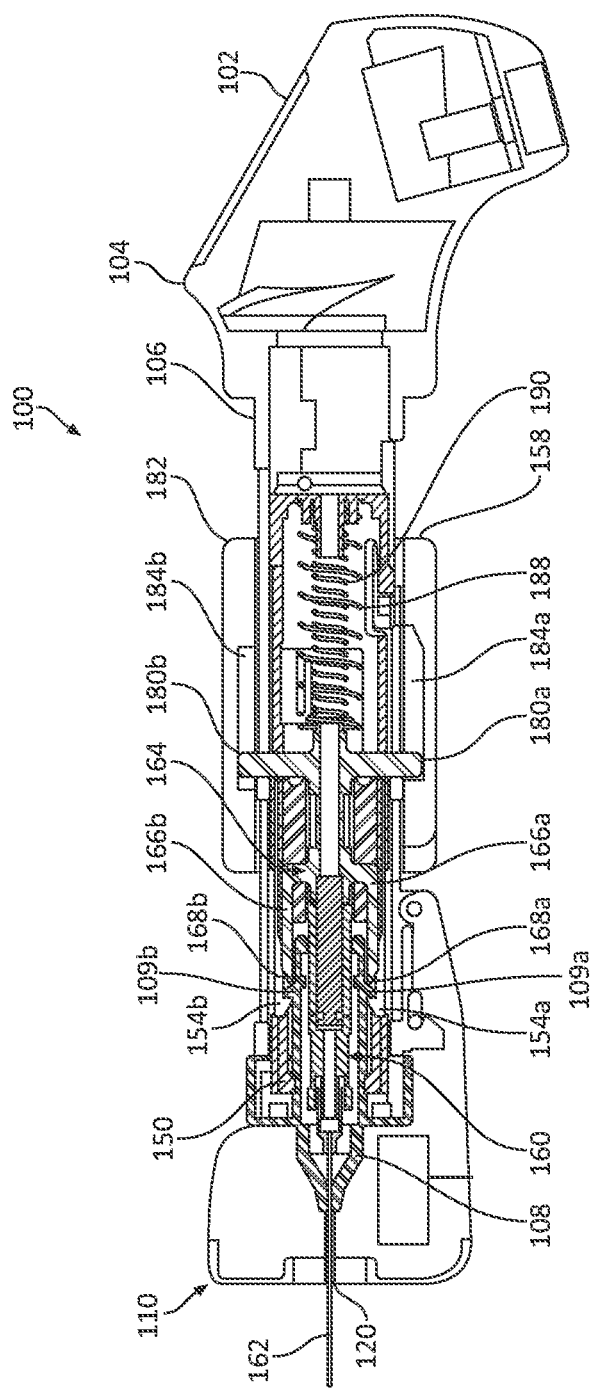
FIG. 9 illustrates the surgical instrument of FIG. 2 in a fired state.

With reference to FIGS. 8 and 9, prior to firing the actuator 140 (FIG. 6), the collar 182 is rotated to displace the arms 180a, 180b of the needle subassembly 164 out of the notches 186a, 186b of the collar 182 and into the longitudinal tracks 184a, 184b of the collar 182. As can be appreciated by viewing, for example, FIG. 9, the collar 182 is prevented from moving distally relative to and along the elongated shaft 106 by virtue of an abutting engagement with the housing 112 of the ultrasonic probe 110. As such, the collar 182 acts as a safety by preventing distal movement of the needle assembly 160 relative thereto due to the arms 180a, 180b of the needle subassembly 164 being captured within the notches 186a, 186b of the collar 182. Prior to rotating the collar 182, incidental firing of the actuator 140 (FIG. 6) will not result in the firing of the needle assembly 160.

With the arms 180a, 180b of the needle subassembly 164 disposed within the tracks 184a, 184b of the collar 182, the needle assembly 160 is free to move distally along and relative to the collar 182 but for the locking engagement of the locking member 158 of the inner sheath 150 with the arm 180a of the needle subassembly 164. To deploy the needle assembly 160, the actuator 140 (FIG. 6) is pivoted into engagement with the locking member 158 of the inner sheath 150, which, in turn, moves the locking member 158 of the inner sheath 150 out of locking engagement with the arm 180a of the needle subassembly 164. With the arm 180a of the needle subassembly 164 released from the locking member 158 of the inner sheath 150, the needle actuator 188 is free to push the needle assembly 160 distally relative to the inner sheath 150 to deploy the needle 162 through and distally beyond the ultrasonic transducer 110 and into tissue.

Figure 10:
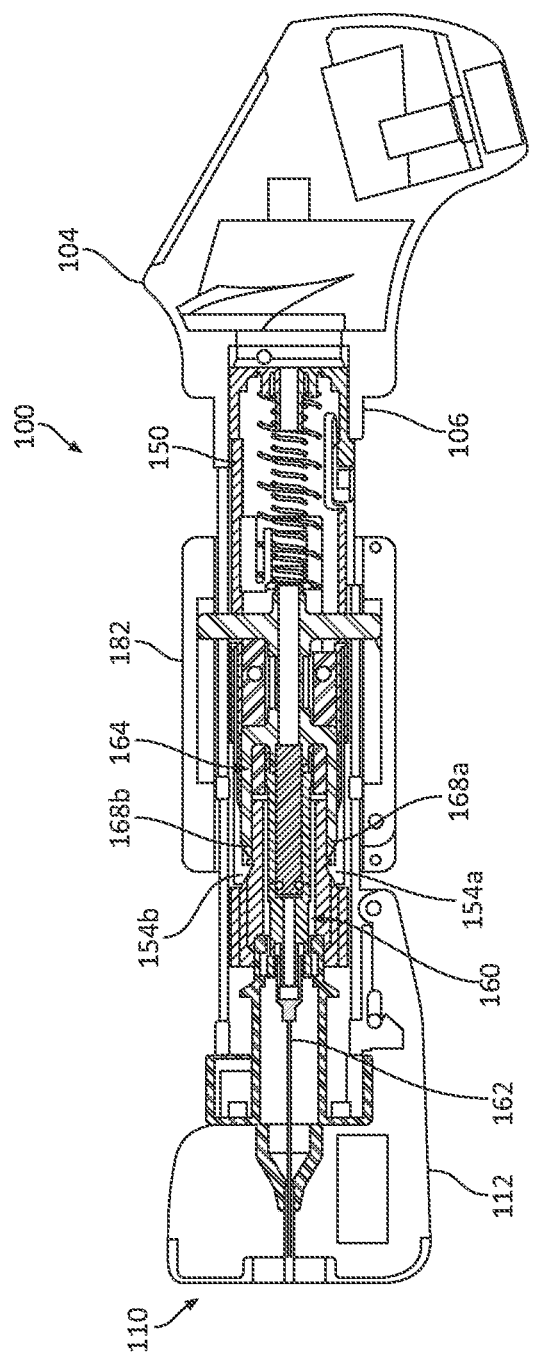
FIG. 10 illustrates the surgical instrument of FIG. 2 in a post-fired state.

As the needle assembly 160 completes its deployment, the ramped distal ends 168a, 168b of the legs 166a, 166b of the needle subassembly 164 concurrently depress the stops 109a, 109b of the needle housing 108 thereby releasing the stops 154a, 154b of the inner sheath 150 from the stops 109a, 109b of the needle housing 108. Upon release of the inner sheath 150 from the needle housing 108, the biasing member 152 (FIG. 6) in the head 104 drives the inner sheath 150 proximally toward the retracted position (as shown in FIG. 10). Proximal movement of the inner sheath 150 causes the needle assembly 160 to be retracted due to the engagement of the stops 154a, 154b of the inner sheath 150 and the ramped distal ends 168a, 168b of the needle subassembly 164. In this way, the needle 162 is immediately and automatically retracted back into the housing 112 of the ultrasonic probe 110 upon finishing its deployment. With tissue captured in the needle 162, a proximal end of the needle subassembly 164 is occluded by the movement driven by actuator 190, thereby creating a passive vacuum in the needle subassembly 164 to hold the tissue sample in the lumen of the needle 162. In embodiments, the tissue may be captured by forming an active vacuum from a plunger (not shown) activated as the needle 162 is retracted back into the housing 112. Needle actuator 152 retracts the inner sheath 150 and all components within it until the needle is completely enclosed behind the distal end of the ultrasound probe 110.

To remove the needle 162 from the needle subassembly 164, the ultrasonic probe 110 may be pivoted relative to the tubular shaft 106 to allow a clinician to gain access to the needle housing 108. The needle housing 108 may then be detached from the tubular shaft 106 by, e.g., unscrewing it from the distal end portion of the tubular shaft 106. With the needle housing 108 detached from the tubular shaft 106, the needle 162 is accessible by a clinician and may be removed from the surgical instrument 100. With the needle 162 removed, the tissue sample may be extracted from the needle 162 and a new, sterile needle may be loaded into the surgical instrument 100 in preparation of reuse of the surgical instrument 100.

In embodiments, the surgical instrument is configured to automatically calculate the depth of the tumor and set the depth at which the needle 162 penetrates the tumor based on the calculated depth of the tumor.

With reference to FIGS. 11-16B, embodiments of a tissue marker 200, 300, and 400 that are deployable using the surgical instrument 100 of FIGS. 1-10 will be described. It is contemplated that the tissue markers 200, 300, 400 may be utilized with any other suitable surgical instrument or deployed without the assistance of a surgical instrument.

With specific reference to FIGS. 11-14, the tissue marker 200 has an elongated configuration and a length sufficient to allow a proximal end of the tissue marker 200 to protrude from an access opening "O" in a skin surface "SS" of a patient while a distal tip 202 of the tissue marker 200 is within a central location of a breast. For example, the tissue marker 200 may have a length between approximately 15 cm and approximately 20 cm. In embodiments, the tissue marker 200 may have any suitable length. The tissue marker 200 has a distal portion 204 having a distal tip 202 configured for penetrating tissue. The distal tip 202 may be fabricated from a metal or a synthetic polymeric material. The tissue marker 200 has a diameter between approximately 2 mm and approximately 3 mm, such that the tissue marker 200 is capable of receipt within the needle 162 of the surgical instrument 100 (FIGS. 1-10), although other diameters are also contemplated.

Figure 11:
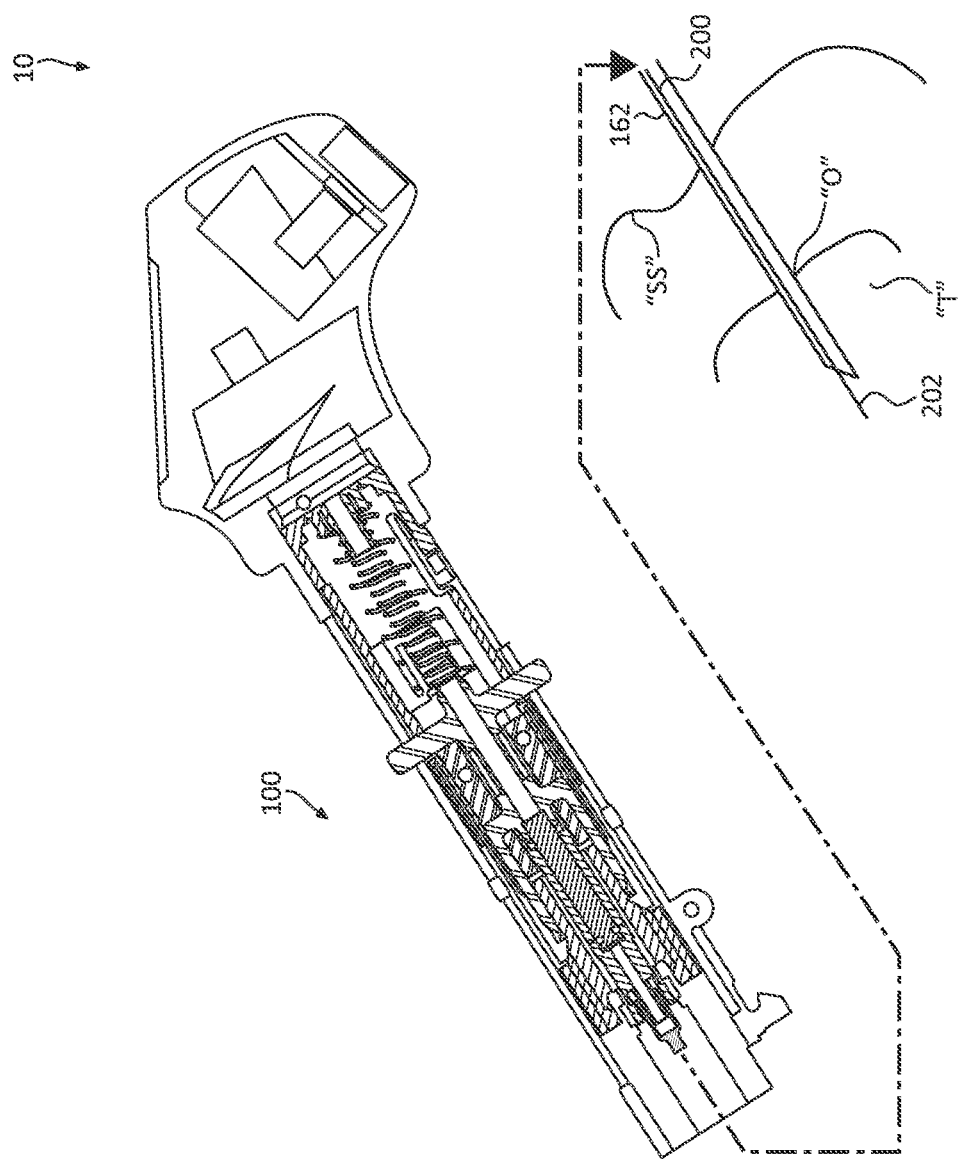
FIG. 11 is a perspective view of a surgical assembly including the surgical instrument of FIG. 1 and a deployable tissue marker coupled to the surgical instrument, in accordance with the present disclosure.
Figure 12B:
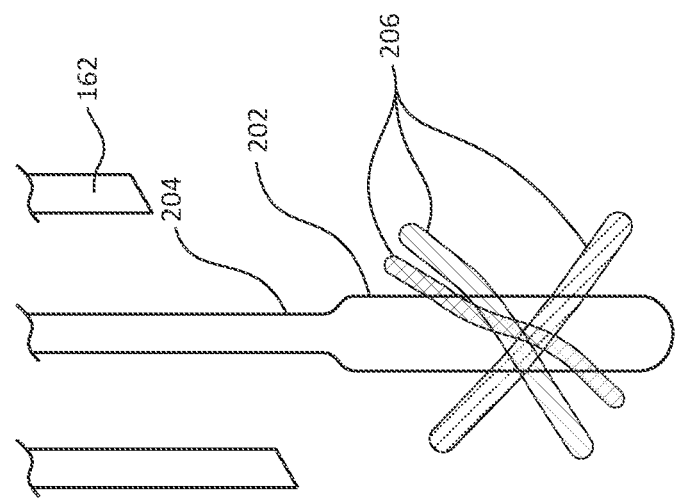
FIG. 12B is a longitudinal cross-sectional view of the distal portion of the tissue marker in an expanded configuration.
Figure 12A:
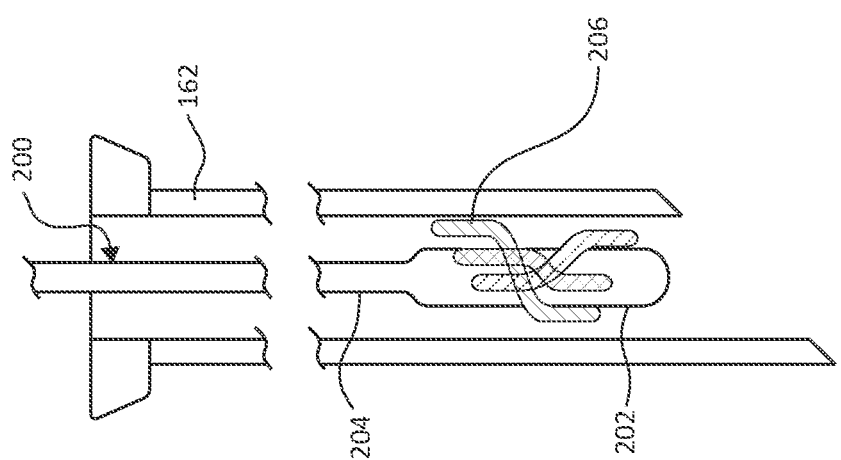
FIG. 12A is a longitudinal cross-sectional view of a distal portion of the tissue marker of FIG. 11 disposed within the needle of the surgical instrument of FIG. 11.

As shown in FIGS. 11 and 12A, the tissue marker 200 is disposed within the needle 162 of the surgical instrument 100 and is deployable therefrom. The tissue marker 200 includes a plurality of fixation elements 206 coupled to the distal tip 202 of the tissue marker 200. The fixation elements 206 are rod-shaped and configured to penetrate tissue to anchor the tissue marker 200 in the tissue. Each of the fixation elements 206 may have a diameter of less than 1 mm (e.g., 0.05 mm to 0.99 mm) but it is contemplated that the fixation elements 206 may have a larger diameter than 1 mm. In embodiments, the fixation elements 206 may assume any shape suitable for penetrating tissue, such as, for example, harpoon-shaped, spiked, hooked, or the like.

The fixation elements 206 are movable between a collapsed state, as shown in FIG. 12A, and an expanded state, as shown in FIG. 12B. In the collapsed state, the fixation elements 206 may be disposed within the distal tip 202 of the tissue marker 200 and/or extend along an outer surface of the distal tip 202 in parallel orientation relative thereto. In the collapsed state, the fixation elements 206 may fit within the needle 162 of the surgical instrument 100 and allow for slidable movement of the tissue marker 200 therein. In the expanded configuration, the fixation elements 206 protrude radially outward from the distal tip 202 of the tissue marker 200 to anchor the tissue marker 200 in tissue. With the fixation elements 206 anchored in tissue, for example, a tumor, a surgeon will have the ability to manipulate the tumor by moving the portion of the tissue marker 200 that protrudes from the skin surface "SS."

The fixation elements 206 may be resiliently biased toward the expanded configuration, such that the fixation elements 206 automatically move to the expanded configuration upon exiting the needle 162. However, when received in the needle 162, the needle 162 prevents the fixation elements 206 from expanding under their resilient bias. It is contemplated that in their expanded configuration, the fixation elements 206 may extend at a perpendicular angle or any suitable angle relative to a longitudinal axis of the tissue marker 200. In embodiments, the fixation elements 206 may each extend at different, random angles relative to the longitudinal axis of the tissue marker 200.

In another embodiment, the fixation elements 206 may be fabricated from shape memory materials, such as, for example, nickel titanium. The shape memory materials automatically change shape upon being warmed by heat of a patient's tissue to change the fixation elements 206 from the collapsed configuration to the expanded configuration.

Figure 13:
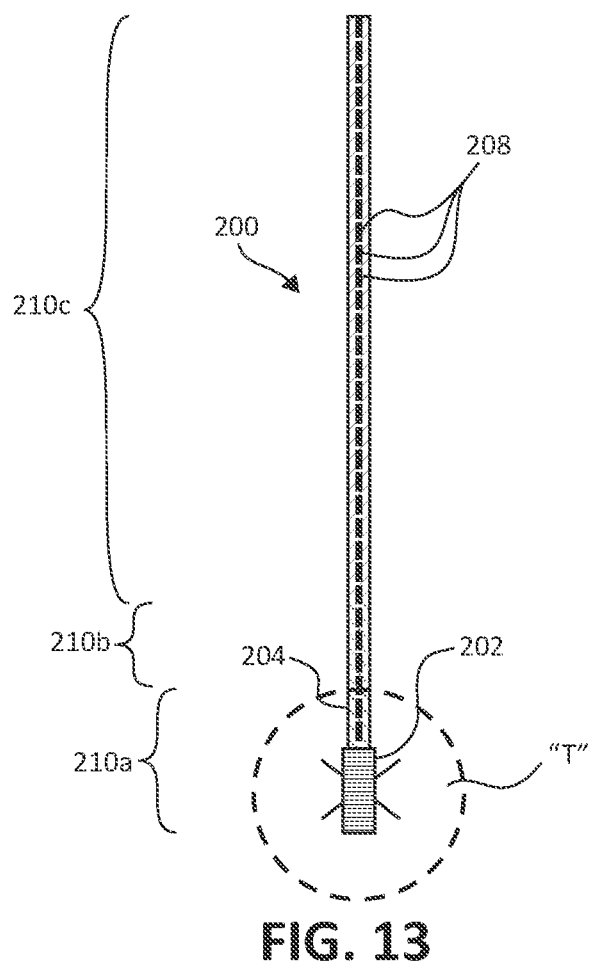
FIG. 13 is a side view of the tissue marker of FIG. 12 illustrating a plurality of markings and discrete longitudinal segments.

With reference to FIG. 13, the tissue marker 200 further includes a plurality of markings 208 disposed along a length thereof to provide a surgeon with a visual reference of the depth of insertion of the tissue marker 200 in the tissue. The markings 208 may be uniformly distanced from one another along the longitudinally axis of the tissue marker 200. For example, the markings 208 may be distanced approximately between 0.1 mm and approximately 10 mm from one another. In other embodiments, one marking 208 may be spaced approximately 1 mm from an adjacent marking 208. The markings 208 may be ultrasound visible, bubbled, and/or abraded. In some embodiments, each of the markings 208 may be circular and extend around the longitudinal axis of the tissue marker 200.

The tissue marker 200 also includes a plurality of longitudinally-extending segments 210a, 210b, 210c disposed along the length of the tissue marker 200. Each of the segments 210a, 210b, 210c has a discrete color or other visually-identifying feature associated therewith that serves to indicate the depth of insertion of the tissue marker 200 in the tissue. For example, a distal segment 210a of the plurality of segments may have a red color, an intermediate segment 210b of the plurality of segments may have a yellow color, and a proximal segment 210c of the plurality of segments may have a green color. As such, the colored segments 210a-c give a surgeon a visual indication of the approximate depth of penetration of the distal tip 202 of the tissue marker 200. In embodiments, the segments 210a-c may have any suitable color or shading to assist in determining tissue depth of the tissue marker 200. In embodiments, rather than having discretely-colored segments 210a-c, the tissue marker 200 may have a color gradient along its length. The tissue marker 200 may have a protrusion disposed between the distal and intermediate segments 210a, 210b to provide a tactile guide for a surgeon.

Figure 13A:
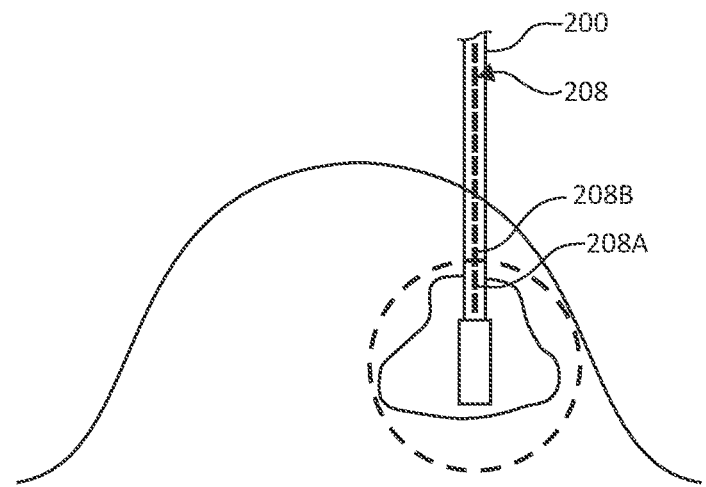
FIG. 13A is a side view of the tissue marker of FIG. 12 illustrating the tissue marker anchored in a tumor.
Figure 13B:
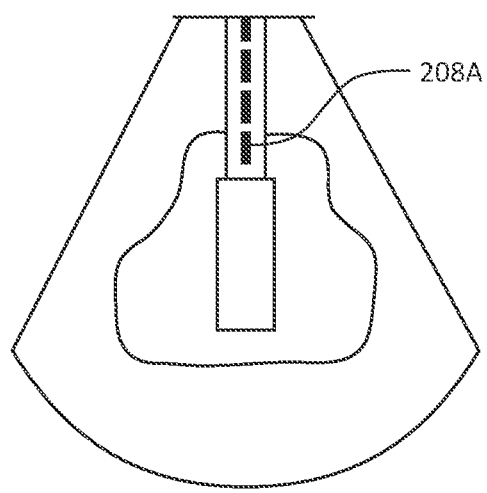
FIG. 13B is an enlarged view of the tissue marker anchored in the tumor.

With reference to FIGS. 13A and 13B, the image of the markings 208 will be captured at the extent of the tissue marker 200 deployment in the ultrasound image, as shown in FIG. 13B. The captured image enables the surgeon to identify the specific marking, such as, for example, marking 208A at the proximal extent of the target tumor and plan an excision to achieve a clear margin around the tumor that will begin at a selected marking, such as, for example, marking 208B. In the surgical procedure that follows, the surgeon will dissect down the shaft of the tissue marker 200 to the marking 208B and then dissect lateral to excise the planned margin around the tumor. By maintaining the dissection path away from the tumor, the surgeon avoids spreading tumor cells into the exposed healthy tissue.

In another embodiment, the shaft of the needle 162 may extend beyond the distal tip or anchor 202 of the tissue marker 200 with additional markings 208 distal of the anchor 202 for locating and excising the distal most aspect of the tumor.

Figure 14:
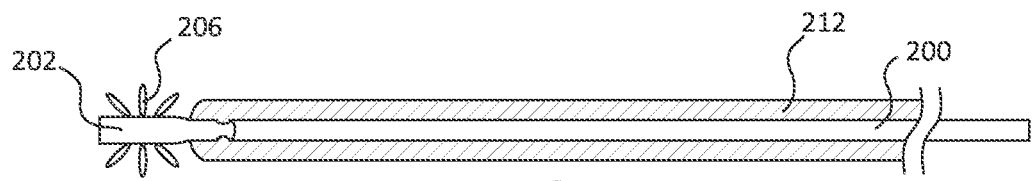
FIG. 14 is a longitudinal cross-sectional view of the tissue marker of FIG. 12 having a sheath disposed thereabout.

With reference to FIG. 14, the surgical assembly 10 may further include a sheath 212 detachably coupled to the tissue marker 200. The sheath 212 may define a longitudinally-extending channel dimensioned for receipt of the tissue marker 200. The sheath 212 may be stiffer than the tissue marker 200 to assist a surgeon in manipulating the tissue marker 200 while the tissue marker 200 is lodged in tissue.

In operation, with reference to FIGS. 11, 12A and 12B, the surgical assembly 10 may be used to mark a tumor in breast tissue in preparation of a lumpectomy. The surgical instrument 100 of the surgical assembly 10 is actuated in the manner described above with reference to FIGS. 1-10 to deploy the needle 162 into the tumor. Since the tissue marker 200 of the surgical assembly 10 is disposed within the needle 162, and a distally-oriented wall in a proximal end of the needle 162 is in abutment with a proximal end of the tissue marker 200, the tissue marker 200 moves with the needle 162 as the needle 162 is advanced distally through breast tissue and into the tumor.

After the needle 162 and the tissue marker 200 penetrate the tumor, the needle 162 is retracted, in the manner described above with reference to FIGS. 1-10. Since the tissue marker 200 is slidably received within the needle 162 and not fixed thereto, the tissue marker 200 does not move proximally with the needle 162 during the proximal acceleration of the needle 162 out of the tumor. As such, the retraction of the needle 162 results in the deployment of the tissue marker 200 therefrom and into the tumor. Upon the distal tip 202 of the tissue marker 200 exiting the needle 162, the fixation elements 206 move from the collapsed configuration to the expanded configuration to anchor the tissue marker 200 in the tumor. In some embodiments, the surgical instrument 100 may include a drive mechanism operably coupled to the tissue marker 200 configured to selectively deploy the tissue marker 200 from the needle 162 of the surgical instrument 100.

In embodiments, the surgical instrument 100 may capture an image of the distal tip 202 of the tissue marker 200 upon deployment into the tumor. The surgical instrument 100 may image the deployment in two planes either simultaneously or sequentially by rotating sensors in the surgical instrument 100 or by having four sensors in two planes. In some embodiments, the surgical instrument 100 may be rotated to take a second image before deploying the tissue marker 200.

Figure 15A:
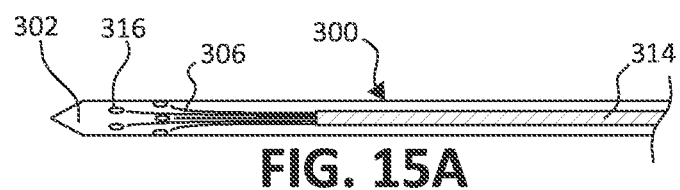
FIG. 15A is a longitudinal cross-sectional view of a tissue marker in accordance with the present disclosure having deployable fixation elements.
Figure 15B:
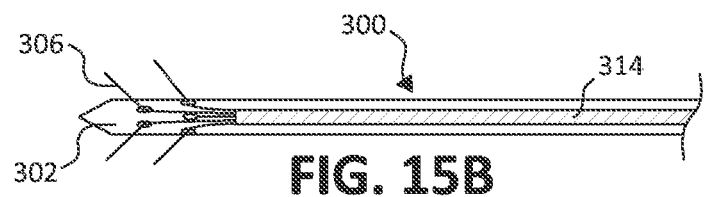
FIG. 15B is a longitudinal cross-sectional view of the tissue marker of FIG. 15A illustrating the fixation elements in an expanded configuration.

With reference to FIGS. 15A and 15B, another embodiment of a tissue marker 300, similar to the tissue marker 200, is illustrated. The tissue marker 300 is different from the tissue marker 200 with respect to its fixation elements 306, and in that it does not require a needle to be deployed. In particular, the fixation elements 306, rather than being resiliently-biased or fabricated from shape memory materials, are deployable via a pull wire 314. Since the fixation elements 306 are deployable via a pull wire 314, the surgical instrument 100 is not required for its usage. The pull wire 314 is coupled to each of the fixation elements 306 to move the fixation elements 306 through holes 316 defined in the distal tip 302 of the tissue marker 300. To deploy the fixation elements 306, the pull wire 314 is moved distally, whereby the fixation elements 306 are moved through the holes 316 in the distal tip 302 and into tissue, as shown in FIG. 15B. Alternatively, proximal actuation or rotational actuation of the pull wire 314 may be effected to deploy the fixation elements 306.

In operation, the surgical instrument 100 may be utilized to deploy the tissue marker 300 into a tumor. In other embodiments, the tissue marker 300 may be deployed into a tumor without the assistance of the surgical instrument 100. The needle 162 of the surgical instrument 100 is replaced with the tissue marker 300 such that the distal tip 302 and the pull wire 314 of the tissue marker 300 are engaged to the needle subassembly 164 of the surgical instrument rather than the needle 162. The tissue marker 300 moves with the needle subassembly 164 as the needle subassembly 164 is advanced distally, whereby the tissue marker 300 penetrates a tumor.

Since the tissue marker 300 is detachably coupled to the needle subassembly 164, the tissue marker 300 does not move proximally with the needle subassembly 164 during the proximal retraction of the needle subassembly 164. As such, the retraction of the needle subassembly 164 results in the detachment of the tissue marker 300 therefrom and the deployment of the tissue marker 300 into the tumor. More specifically, after the tissue marker 300 penetrates the tumor, the needle subassembly 164 is retracted, in the manner described above with reference to FIGS. 1-10. For example, when the tissue marker 300 reaches its final depth, the pull wire 314 is pushed further, while the distal tip 302 remains steady. This deploys the fixation elements 316 and keeps the tissue marker 300 in the exact same location relative to the target tissue (e.g. tumor). After anchoring the fixation elements 316 in the tumor, both the distal tip 302 and the pull wire 314 are released from the needle subassembly 164, so the whole tissue marker 300 remains now detached from the instrument 100. In embodiments, since the pull wire 314 extends proximally out of the patient's skin surface, a clinician may manually manipulate the pull wire 314. In particular, the pull wire 314 is moved distally, whereby the fixation elements 306 are moved through the holes 316 in the distal tip 302 and into the tumor to anchor the tissue marker 300 in the tumor.

Figure 16A:
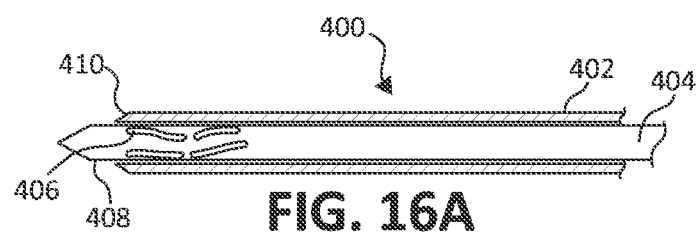
FIG. 16A is a longitudinal cross-sectional view of another tissue marker in accordance with the present disclosure having fixation elements that move from a collapsed configuration to an expanded configuration.
Figure 16B:
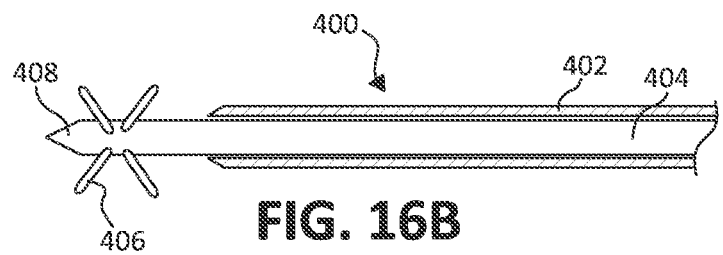
FIG. 16B is a longitudinal cross-sectional view of the tissue marker of FIG. 16A illustrating the fixation elements thereof in an expanded configuration.

With reference to FIGS. 16A and 16B, another embodiment of a tissue marker 400, similar to the tissue marker 200, is illustrated. The tissue marker 400 includes an outer tube 402 that surrounds a rod member 404. The rod member 404 has fixation elements 406 attached to a tissue-penetrating distal tip 408 of the rod member 404. The fixation elements 406 may be fabricated from shape memory materials or may be resiliently biased toward an expanded configuration. The outer tube 402 captures the rod member 404 therein and maintains the fixation elements 406 in a collapsed configuration until the outer tube 402 is partially retracted relative to the rod member 404 to expose the fixation elements 406. The outer tube 402 may have a distal tip 410 configured to penetrate tissue, e.g., the distal tip 410 may be beveled.

In operation, the surgical instrument 100 may be utilized to deploy the tissue marker 400 into a tumor. In other embodiments, the tissue marker 400 may be deployed into a tumor without the assistance of the surgical instrument 100. The needle 162 of the surgical instrument 100 is replaced with the tissue marker 400 such that the tissue marker 400 is operably coupled to the needle subassembly 164 of the surgical instrument 100 rather than the needle 162. The tissue marker 400 moves with the needle subassembly 164 as the needle subassembly 164 is advanced distally, whereby the tissue marker 400 penetrates a tumor.

After the tissue marker 400 penetrates the tumor, the needle subassembly 164 is partially retracted, in the manner described above with reference to FIGS. 1-10. Since the tissue marker 400 is detachably coupled to the needle subassembly 164, the tissue marker 400 does not move proximally with the needle subassembly 164 during the proximal retraction of the needle subassembly 164. As such, the retraction of the needle subassembly 164 results in the detachment of the tissue marker 400 therefrom and the deployment of the tissue marker 400 into the tumor. For example, prior to the needle subassembly 164 releasing the tissue market 400, the rod member 404 remains in the exact deployment position, and the outer tube 402 retracts.

With the tissue marker 400 disposed within the tumor, the outer tube 402 and/or the rod member 404 of the tissue marker 400 extends proximally out of the patient's skin surface to allow a clinician to manipulate the tissue marker 400. In particular, the outer tube 402 is moved proximally relative to the rod member 404 to expose the fixation elements 406, whereby the fixation elements 406 are moved from the collapsed configuration to the expanded configuration and into the tumor to anchor the tissue marker 400 in the tumor.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of marking a tumor, comprising:
    positioning a surgical instrument adjacent breast tissue;
    generating an image of a tumor in the breast tissue on a display using an ultrasonic probe of the surgical instrument while the ultrasonic probe is in a first rotational orientation relative to a longitudinal axis defined by the ultrasonic probe;
    rotating the ultrasonic probe about the longitudinal axis from the first rotational orientation to a second rotational orientation and generating another image of the tumor in the breast tissue on the display using the ultrasonic probe of the surgical instrument while the ultrasonic probe is in the second rotational orientation;
    aligning a needle of the surgical instrument with the tumor using the image and the another image of the tumor generated on the display;
    deploying the needle from the ultrasound probe into the breast tissue;
    deploying an elongated tissue marker from the needle into the tumor, thereby fixing a distal portion of the tissue marker in the tumor; and
    transitioning a plurality of fixation elements of the tissue marker from a collapsed state into an expanded state, in which the plurality of fixation elements anchor into the tumor, wherein one fixation element of the plurality of fixation elements extends through a central longitudinal axis defined by a distal tip of the tissue marker and has a first end portion disposed at a first side of the central longitudinal axis of the distal tip when the one fixation element is in the expanded state, and a second end portion disposed at an opposite second side of the central longitudinal axis of the distal tip when the one fixation element is in the expanded state, the first end portion being disposed proximally of the second end portion.

2. The method according to claim 1, further comprising generating an image of both the tumor and the elongated tissue marker while the elongated tissue marker is fixed in the tumor.

3. The method according to claim 2, further comprising planning a surgical excision of the tumor based on a position of a first depth marking on the elongated tissue marker relative to an outer periphery of the tumor.

4. The method according to claim 3, further comprising excising the tumor at a location adjacent a second depth marking of the elongated tissue marker, wherein the second depth marking is disposed proximally of the first depth marking.

5. The method according to claim 1, further comprising retracting the needle from the breast tissue and into the ultrasonic probe.

6. The method according to claim 5, wherein the retraction of the needle causes the tissue marker to deploy from the needle.

7. The method according to claim 5, wherein the tissue marker is deployed from the needle prior to the needle being retracted.

8. The method according to claim 1, wherein the plurality of fixation elements transition toward the expanded state automatically upon deployment from the needle.

9. The method according to claim 8, wherein the plurality of fixation elements are fabricated from shape memory material, such that the plurality of fixation elements transition toward the expanded state in response to heat from the breast tissue.

10. The method according to claim 8, wherein the plurality of fixation elements are resiliently biased toward the expanded state and maintained in the collapsed state by the needle.

11. The method according to claim 1, further comprising determining a distance between an access opening in the breast tissue and the distal tip of the tissue marker using a plurality of longitudinally-extending segments disposed along a length of the tissue marker, each of the plurality of segments having a discrete visually identifying feature.

12. A method of marking a tumor, comprising:
generating an image of a tumor in breast tissue using an ultrasonic probe;
aligning an elongated tissue marker with the tumor using the image of the tumor;
deploying the tissue marker from the ultrasonic probe into the tumor; and
transitioning a plurality of fixation elements of the tissue marker from a collapsed state into an expanded state to fix a distal portion of the tissue marker in the tumor, wherein one fixation element of the plurality of fixation elements extends through a central longitudinal axis defined by a distal tip of the tissue marker and has a first end portion disposed at a first side of the central longitudinal axis of the distal tip when the one fixation element is in the expanded state, and a second end portion disposed at an opposite second side of the central longitudinal axis of the distal tip when the one fixation element is in the expanded state, the first end portion being disposed proximally of the second end portion.

13. The method according to claim 12, further comprising retracting an outer member of the tissue marker from the breast tissue.

14. The method according to claim 13, wherein the retraction of the outer member of the tissue marker allows the plurality of fixation elements to transition toward the expanded state.

15. The method according to claim 13, wherein the plurality of fixation elements are fabricated from shape memory material, such that the plurality of fixation elements transition toward the expanded state in response to heat from the breast tissue.

16. The method according to claim 13, wherein the plurality of fixation elements are resiliently biased toward the expanded state and maintained in the collapsed state by the outer member.

17. The method according to claim 12, wherein the plurality of fixation elements transition toward the expanded state automatically upon deployment from a needle of the ultrasonic probe.

18. The method according to claim 12, further comprising determining a distance between an access opening in the breast tissue and the distal tip of the tissue marker using a plurality of longitudinally-extending segments disposed along a length of the tissue marker, each of the plurality of segments having a discrete visually identifying feature.

19. A method of marking a tumor, comprising:
inserting an elongated tissue marker into a tumor disposed in breast tissue; and
transitioning a plurality of fixation elements of the tissue marker from a collapsed state into an expanded state, in which the plurality of fixation elements anchor a distal portion of the tissue marker in the tumor, wherein one fixation element of the plurality of fixation elements extends through a central longitudinal axis defined by a distal tip of the tissue marker and has a first end portion disposed at a first side of the central longitudinal axis of the distal tip when the one fixation is in the expanded state, and a second end portion disposed at an opposite second side of the central longitudinal axis of the distal tip when the one fixation is in the expanded state, the first end portion being disposed proximally of the second end portion.

20. The method according to claim 19, wherein the plurality of fixation elements are fabricated from shape memory material, such that the plurality of fixation elements transition toward the expanded state in response to heat from the breast tissue.

21. The method according to claim 19, wherein the plurality of fixation elements are resiliently biased toward the expanded state.

22. The method according to claim 19, further comprising determining a distance between an access opening in the breast tissue and the distal tip of the tissue marker using a plurality of longitudinally-extending segments disposed along a length of the tissue marker, each of the plurality of segments having a discrete visually identifying feature.

* * * * *